United States Patent [19]

Karrer

[11] 4,048,235
[45] Sept. 13, 1977

[54] PROPENYLOXY BENZENE COMPOUNDS

[75] Inventor: Friedrich Karrer, Basel, Switzerland

[73] Assignee: Ciba-Geigy Corporation, Ardsley, N.Y.

[21] Appl. No.: 590,658

[22] Filed: June 26, 1975

Related U.S. Application Data

[63] Continuation-in-part of Ser. No. 340,806, March 13, 1973, abandoned.

[30] Foreign Application Priority Data

Mar. 16, 1972 Switzerland .......................... 3935/72
Feb. 16, 1973 Switzerland .......................... 2327/73

[51] Int. Cl.$^2$ ............................................. C07C 43/27
[52] U.S. Cl. .............................. 260/612 R; 260/613 R; 424/340; 424/341
[58] Field of Search .................... 260/612 R, 613 R

[56] References Cited

U.S. PATENT DOCUMENTS

| | | | |
|---|---|---|---|
| 2,248,491 | 7/1941 | Coleman et al. ................. | 260/613 R |
| 3,162,615 | 12/1964 | Bremmer ........................ | 260/613 R X |
| 3,548,009 | 12/1970 | Priddy et al. .................... | 260/613 R |
| 3,907,783 | 9/1975 | Pallos ............................ | 260/612 R X |

FOREIGN PATENT DOCUMENTS 796,809  9/1973  Belgium

OTHER PUBLICATIONS

Sarmiento, Science, vol. 179, (1973), p. 1342.
Pawson et al., Insect Juvenile Hormones, (1972), pp. 191–214.
Slama, Annual Rev. of Biochemistry, vol. 40, (1971), pp. 1079–1102.
Borkovec, Insect Chemosterilants, (1966), pp. 61–63.
Slama et al., Proc. National Academy of Sciences, vol. 54, (1965), pp. 411–414.

Primary Examiner—Bernard Helfin
Attorney, Agent, or Firm—Harry Falber

[57] ABSTRACT

Compounds of the formula

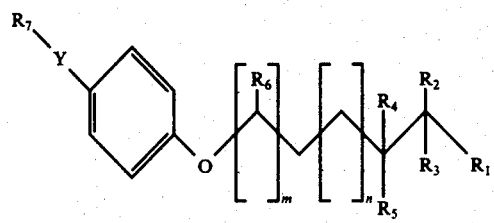

wherein
$R_1$ represents hydrogen, halogen, $C_1$-$C_4$-alkyl or vinyl,
$R_2$ represents hydrogen, halogen, methyl or ethyl,
$R_3$ represents hydrogen, halogen, methyl or $C_1$-$C_4$-alkoxy,
$R_4$ represents hydrogen, halogen or methyl,
$R_5$ represents hydrogen, or $R_3$ and $R_5$ together represent a carbon-carbon bond,
$R_6$ represents hydrogen or methyl,
$R_7$ represents cyclohexyl or the group

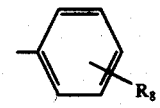

wherein
$R_8$ represents hydrogen, halogen, $C_1$-$C_4$-alkyl or $C_1$-$C_4$-alkoxy, and
Y represents —$CH_2$— or a direct bond, and
$m$ and $n$ each represent the number 0 or 1.

3 Claims, No Drawings

PROPENYLOXY BENZENE COMPOUNDS

CROSS REFERENCES

This application is a continuation-in-part of co-pending application Ser. No. 340,806 Mar. 13, 1973 and now abandoned.

The invention relates to aryl ether derivatives, to their production, and to their use for the control of insects. The compounds correspond to the formula

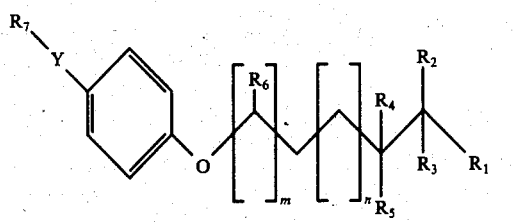

wherein
$R_1$ represents hydrogen, halogen, $C_1$-$C_4$-alkyl or vinyl
$R_2$ represents hydrogen, halogen, methyl or ethyl,
$R_3$ represents hydrogen, halogen, methyl or $C_1$-$C_4$-alkoxy,
$R_4$ represents hydrogen, halogen or methyl,
$R_5$ represents hydrogen, or $R_3$ and $R_5$ together represent a carbon-carbon bond,
$R_6$ represents hydrogen or methyl,
$R_7$ represents cyclohexyl or the group

wherein
$R_8$ represents hydrogen, halogen $C_1$-$C_4$-alkyl or $C_1$-$C_4$-alkoxy, and
Y represents —$CH_2$— or a direct bond, and
m and n each represent the number 0 or 1.

Halogen is fluorine, chlorine, bromine or iodine, particularly chlorine.

The alkyl and alkoxy groups in the case of $R_1$, $R_3$ and $R_8$ can be straight-chain or branched. Examples of such groups include methyl, ethyl, propyl, isopropyl, i-, n-, sec.-, tert.- butyl, methoxy and ethoxy.

Compounds of formula I to be emphasised are those wherein
$R_1$ represents hydrogen, chlorine, methyl, ethyl or vinyl,
$R_2$ represents hydrogen, chlorine or methyl,
$R_3$ represents hydrogen, chlorine, methyl, ethyl, methoxy or ethoxy,
$R_4$ represents hydrogen, chlorine or methyl,
$R_5$ represents hydrogen, or $R_3$ or $R_5$ together represent a carbon-carbon bond,
$R_6$ represents hydrogen or methyl,
$R_7$ represents cyclohexyl or the group

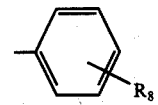

wherein
$R_8$ represents hydrogen, chlorine, methyl or methoxy, and
Y represents —$CH_2$— or a direct bond, and
m and n each represent the number 0 or 1.

Compounds of formula I which are preferred on account of their action are such compounds wherein
$R_1$ represents hydrogen, chlorine, methyl, ethyl or vinyl,
$R_2$ represents hydrogen, chlorine or methyl,
$R_3$ represents hydrogen or methoxy,
$R_4$ represents hydrogen, chlorine or methyl,
$R_5$ represents hydrogen, or $R_3$ and $R_5$ together represent a carbon-carbon bond,
$R_6$ represents hydrogen or methyl,
$R_7$ represents cyclohexyl or the group

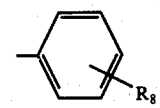

wherein
$R_8$ represents hydrogen, chlorine or methyl, and
Y represents —$CH_2$— or a direct bond, and
m and n each represent the number 0 or 1.

The compounds of formula I are produced in a manner known per se by the following methods:

1. Formation of the ether (O-alkylation) by condensation of a halide of formula III with a compound of formula II:

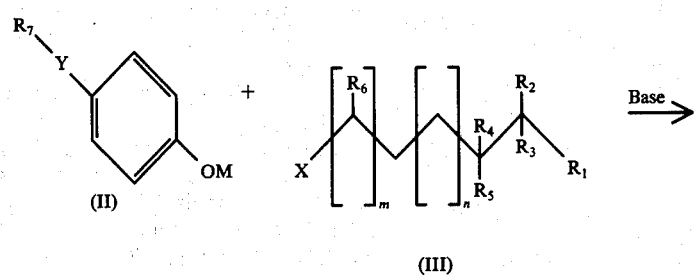

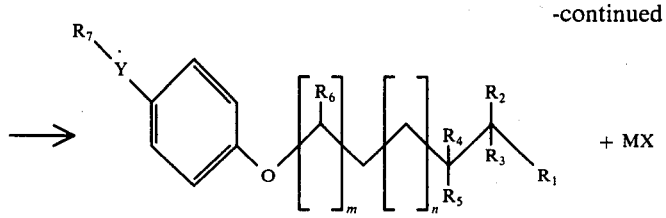

(I)

whereby in formulae II and III, the symbols $R_1$ to $R_7$, Y, m and n have the meanings given for formula I; X stands for chlorine, bromine or iodine, preferably for chlorine or bromine; M is a metal, especially the I. or II. main group of the periodic system, or hydrogen.

The mercury(II)-salts preferably used are mercury acetate or mercury trifluoroacetate.

3. Alkylation of an alcohol of formula IG

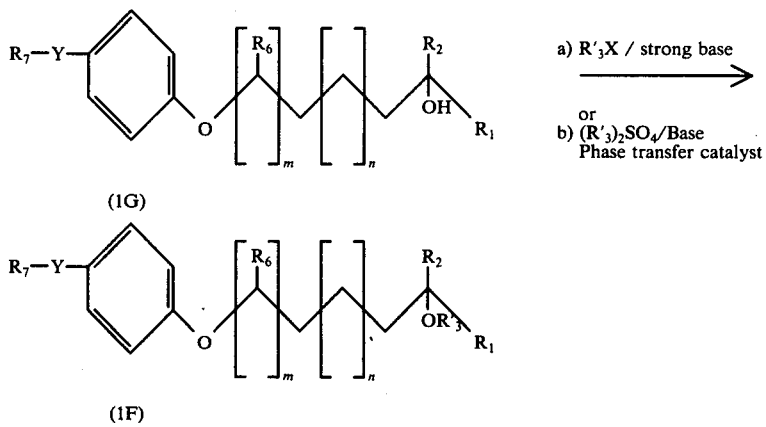

whereby $R_1$, $R_2$, $R_4$, $R_6$, $R_7$, Y, m and n have the meanings given for formula I, X represents a halogen atom, and $R'_3$ a $C_1$-$C_4$-alkyl radical, or The reaction may also be effected by $(R_3')_2SO_4$ in alkali hydroxide solution in the presence of a phase transfer catalyst such as tetraalkyl ammonium halide such as tetrabutyl ammonium iodide.

The O-alkylation of a compound of formula II can be performed with the various saturated or unsaturated halides, depending on the reactivity of the applied halide, in various solvents and at various reaction temperatures — always, however, in the presence of at least one mole of one of the bases mentioned below.

Suitable inert solvents are, in particular, acetone, methyl, ethyl ketone, cyclohexanone, 1,2-dimethoxyethane, tetrahydrofuran, dioxane, dialkyl ether, dimethylformamide, dimethylsulphoxide, hexamethylphosphoric acid triamide, sulpholane, inert hydrocarbons such as toluene, benzene, xylene, and so forth. It is possible, however, also to use other solvents.

The necessary bases and acid acceptors, respectively, are, in particular alkali or alkaline-earth hydroxides, alkali alkoxides; it is possible, however, to use organic bases such as, e.g. triethylamine, pyridine, and so forth, as acid acceptors.

The reaction temperatures for ether formation are between $-10°$ and 130° C, mostly between 5° and 75° C (e.g. with application of solvents such as dimethylsulphoxide, dimethylformamide, dioxane, sulpholane, tetrahydrofuran, hexamethylphosphoric acid triamide, 1,2-dimethoxyethane, etc.); or the reaction is performed at the boiling temperature of the employed solvent (e.g. in the case of ketones).

The processing and isolation of compounds of formula I, are effected by known techniques; e.g., addition of water or ice to the reaction mixture; subsequent extraction with a suitable solvent, e.g. ether; washing of the organic phase, e.g. with dilute alkali solution or alkali carbonate; and drying of the solution over anhydrous sodium sulphate. After removal of the solvent, the obtained compound of formula I can, if necessary, be purified by crystallisation, vacuum distillation, or chromatography on silica gel or aluminium oxide.

The reactions to the active substance of formula I wherein $R_3$ represents a $C_1$-$C_4$-alkoxy group are performed at normal pressure and in an anhydrous alcohol $R'_3OH$, and, optionally, in solvents and diluents inert to the reactants, e.g. in ethers such as tetrahydrofuran, dioxane, diethyl ether, 1,2-dimethyloxyethane, etc..

In the 1st step —if $R'_3=H$ — as well as in the 2nd step, it is also possible to use water as the solvent.

The mercury-(II)-salts preferably used are mercury-(II)-acetate and mercury-(II)-trifluoroacetate. The complex hydride used is, for example, $MeBH_4$, wherein Me represents an alkali metal atom or alkaline-earth metal atom. The reaction with complex hydride is performed in the presence of alkali hydroxide and water. The reaction temperatures are in the range of $-10°$ to $+40°$ C, preferably between 10° and 30° C.

Further methods for the obtainment of compounds of formula I wherein $R_3$ represents a $C_1$-$C_4$-alkoxy group, include also the etherification of an alcohol of formula IG by reaction with a halide, depending on the reactivity of the employed halide, in various solvents and at various reaction temperatures — always, however, in the presence of at least one mole of the above mentioned bases.

The obtained compounds occur, where this is, in principle, possible, as cis/trans-isomer mixtures. An isomer mixture can be separated, e.g. with the aid of chromatographic separation methods, into the isomeric forms; for example, by adsorption on a separating material having selective adsorption activity, such as, e.g. silica gel, aluminium oxide, and subsequent elution of the separated isomers with a suitable solvent such as, e.g. diethyl ether, hexane, methyl or ethyl acetate. A further chromatographic separation method is gas chromatography. In certain cases, an isomer mixture can be separated also by fractional distillation or by fractional crystallisation.

The starting materials are known compounds, which can be produced by methods analogous to known methods described in the literature.

The compounds of formula I are suitable for the control of a wide variety of plant pests; the said compounds are particularly suitable for the control of insects. The new substances can be used, in particular, for the control of larvae and eggs of insects of the following orders and families:

Hemiptera: Miridae, Piesmidae, Lygaeidae, Pyrrhocoridae, Pentatomidae, Cimicidae, Reduviidae, Jassidae, Eriosomatidae, Lecaniidae, Diaspididae. The new substances show especially good activity against insects of the families Pyrrhocoridae and Diaspididae such as *Dysdercus fasciatus* and *Aondiella aurantii.*

Lepidoptera: Pieridae, Pluttellidae, Lymantriidae, Noctuidae such as especially *Spodoptera littoralis.*

Coleoptera: Carabidae, Elateridae, Coccinellidae, Tenebrionidae, Dermestidae, Cucujidae, Chrysomelidae, Curculionidae, Scolytidae, Scarabaeidae, especially representatives of the family Tenebrionidae such as *Tenebrio molitor.*

Diptera: Culicidae, Simuliidae, Tipulidae. Their very good action against representatives of the family Culicidae i.e., mosquito larvae (*aedes aegypti*) it to be particularly emphasised. Moreover the active compounds can be used for the control of mites of the order acarina especially Tetranychidae such as *Tetranychus urticae.*

The action of compounds of formula I can be appreciably broaded, enhanced and adapted to suit given conditions by the addition of other insecticides and/or acaricides.

Suitable additives are, for example known active substances of the following groups: organic phosphorus compounds, nitrophenols and derivatives, pyrethroide, formamidines, urea derivatives, carbamates chlorinated Hydrocarbons.

The agents according to the invention are produced in a manner known per se by the intimate mixing and/or grinding of active substances of formula I with the suitable carriers, optionally with the addition of dispersing agents or solvents which are inert to the active substances. The active substances can be obtained and used in the following preparation forms: solid preparations: dusts, scattering agents, granulates, coated granulates, impregnated granulates and homogeneous granulates.

The compounds of formula I can be used on their own or together with suitable carriers and/or additives. Suitable carriers and additives may be solid or liquid, and correspond to the substances common in formulation practice, such as, e.g. natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays, or solutions, the formulatin of these preparations being effected in a manner commonly known in practice.

liquid preparations:
 a. water dispersible active substance concentrates: wettable powders, pastes, emulsions;
 b. solutions.

The solid preparations (dusts, scattering agents) are produced by the mixing of the active substances with solid carriers. Suitable carriers are, e.g., kaolin, talcum, bole, loess, chal, limestone, ground limestone, attapulgite, dolomite, diatomaceous earth, precipitated silicic acid, alkaline-earth silicates, sodium and potassium aluminium silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

Granulates can be very easily prepared by a process in which an active substance of formula I is dissolved in an organic solvent, the thus obtained solution applied to a granulated minera, e.g. attapulgite, $SiO_2$, granicalcium, bentonite, etc., and the organic solvent then evaporated off.

It is possible also to produce polymer granulates; in this case the active substances of formula I are mixed with polymerisable compounds (urea/formaldehyde; dicyandiamide/formaldehyde; melamine/formaldehyde, or others); polymerisation is then carefully carried out in a manner which leaves the active substances unaffected, and granulation performed actually during the gel forming process. It is more favourable, however, to impregnate finished porous polymer granules (urea/-formaldehyde, polyacrylonitrile, polyester and others), having a specific surface area and a favourable predeterminable adsorption/desorption ratio, with the active substances, e.g. in the form of their solutions (in a low-boiling solvent), and to then remove the solvent. Polymer granulates of this kind can be also sprayed in the form of microgranulates, having bulk weights of preferably 300 g/liter to 600 g/liter, with the aid of spray apparatus. Spraying can be carried out over extensive areas of useful plant crops by the use of aeroplanes.

Granulates can also be obtained by the compacting of the carrier material with the active substances and additives, and a subsequent reducing operation.

Moreover, it is possible to add to these mixtures additives stabilising the active substance and/or nonionic, anion-active and cation-active substances which improve, e.g. the adhesiveness of the active substances on plants and parts of plants (adhesives and agglutinants), and/or ensure a better wettability (wetting agents) as well as dispersibility (dispensing agents).

The following substances are, for example, suitable: olein/lime mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, lignin-sulphonic acid, the alkali metal and alkaline-earth metal salts thereof, polyethylene glycol ethers (carbowaxes), fatty alcohol polyglycol ethers having 5 to 20 ethylene oxide radicals per molecular and 8 to 18 carbon atoms in the fatty alcohol moiety, condensation products of ethylene oxide, propylene oxide, polyvinyl-pyrrolidones, polyvinyl alcohols, condensation products of urea and formaldehyde, as well as latex products.

Water-dispersible concentrates of active substances, i.e. wettable powders, pastes and emulsion concentrates, are agents which can be diluted with water to obtain any desired concentration. They consist of active substance, carrier, optionally additives which stabilise the active substances, surface-active substances, and anti-foam agents and, optionally, solvents.

The wettable powders and pastes are obtained by the mixing and grinding of the active substances with dispersing agents and pulverulent carriers, in suitable devices, until homogeneity is obtained. Suitable carriers are, e.g. those previously mentioned in the case of solid preparations.

It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalene-sulphonic acids with phenol and formaldehyde, as well as alkali, ammonium and alkaline-earth metal salts of ligninsulphonic acid, also alkylarylsulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary ethylene glycols, dialkyl dilauryl ammonium chloride, and fatty acid alkali-metal and alkaline-earth metal salts.

Suitable anti-foam agents are, e.g. silicones.

The active substances are so mixed, ground, sieved and strained with the above mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are, e.g. alcohols, benzene, xylene, toluene, dimethylsulphoxide, and mineral oil fractions boiling in the range of 120° to 350° C. The solvents must be practically odourless, non-phytotoxic, and inert to the active substances.

Furthermore, the agents according to the invention can be used in the form of solutions. For this purpose, the active substance, or several active substances, of the general formula I is dissolved in suitable organic solvents, solvent mixtures, or water. As organic solvents it is possible to use aliphatic and aromatic hydrocarbons, their chlorinated derivatives, alkylnaphthalenes, mineral oils on their own or in admixture with each other.

The content of active substance in the above described agents is between 0.1 and 95%; it is to be mentioned in this connection that in the case of application of the agents from an aeroplane, or by means of some other suitable application devices, concentrations of up to 99.5% can be used, or even the pure active substance.

The active substances of formula I can be prepared, e.g. as follows:

Dusts

The following substances are used for the preparation of (a) a 5% dust, and (b) a 2% dust:

(a)

5 parts of active substance
95 parts of talcum.

(b)

2 parts of active substance
1 part of highly dispersed silicic acid
97 parts of talcum.

The active substances are mixed and ground with the carriers.

Granulate

The following substances are used to produce a 5% granulate:

5 parts of active substance,
0.25 parts of epichlorohydrin,
0.25 parts of cetyl polyglycol ether,
3.50 parts of polyethylene glycol.
91 parts of kaolin (particle size 0.3 - 0.8 mm).

The active substance is mixed with epichlorhydrin and dissolved with 6 parts of acetone; the polyethylene glycol and cetyl polyglycol ether are then added. The thus obtained solution is sprayed on to kaolin, and the acetone subsequently evaporated in vacuo.

Wettable powder

The following constituents are used for the preparation of (a) a 40%, (b) and (c) a 25%, and (d) a 10% wettable powder:

(a)

40 parts of active substance,
5 parts of sodium lignin sulphonate,
1 part of sodium dibutyl-naphthalene sulphonate,
54 parts of silicic acid.

(b)

25 parts of active substance,
4.5 parts of calcium lignin sulphonate
1.9 parts of Champagne chalk/hydroxyethyl cellulose mixture (1:1),
1.5 parts of sodium dibutyl naphthalene sulphonate,
19.5 parts of silicic acid.
19.5 parts of Champagne chalk,
28.1 parts of kaolin.

(c)

25 parts of active substance,
2.5 parts of isooctylphenoxy-polyoxyethylene-ethanol,
1.7 parts of Champagne chalk/hydroxyethyl
8.3 parts of sodium aluminium silicate,
16.5 parts of kieselguhr,
46 parts of kaolin.

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained when can be diluted with water to give suspensions of any desired concentration.

Emulsifiable concentrates

The following substances are used to produce (a) a 10%, (b) a 25% and (c) a 50% emulsifiable concentrate:

(a)

10 parts of active substance,
3.4 parts of epoxidised vegetable oil,
13.4 parts of combination emulsifier consisting of fatty alcohol polyglycol ether and alkylarylsulphonate calcium salt,
40 parts of dimethylformamide,
43.2 parts of xylene.

(b)

25 parts of active substance,
2.5 parts of epoxidised vegetable oil,
10 parts of an alkylarylsulphonate/fatty alcohol-polyglycol ether mixture,
5 parts of dimethylformamide,
57.5 parts of xylene.

(c)

50 parts of active substance,
4.2 parts of tributylphenol-polyglykolether,
5.8 parts of calcium-dodecylbenuolsulphonate,
20 parts of cyclohexanon,
20 parts of xylole.

From these concentrates it is possible to produce, by dilution with water, emulsions of any desired concentration Spray The following constituents are used to prepare (a) a 5% and (b) a 95% spray:

(a)

5 parts of active substance,
1 part of epichlorohydrin,
94 parts of benzine (boiling limits 160° – 190° C).

(b)

95 parts of active substance,
5 parts of epichlorohydrin.

EXAMPLE 1

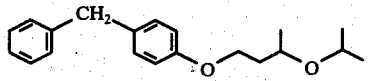

To a suspension [cooled to −2° C] of 57,2 g powdered mercury (II)acetate in 400 ml dry isopropanole — a solution of 43,2 g 1-benzyl-4-(2-butenyl-1-oxy) benzene in 50 ml dry isopropanole are added by vigorously stirring over a period of 10 minutes. A slight raise of the temperature was noted. 14 hours after the addition of the alkene 150 ml 3 N aqueous sodium hydroxide and immediately thereupon a solution of 4,7 g sodium boron hydride in 200 ml 3 N sodium hydroxide are added to the mixture at −2° C, followed by further stirring during 14 hours at normal temperature. The reaction mixture was decanted from the precipitated mercury, the overlying solution poured into the water and the mixture extracted rpeatedly with diethyl ether.

The combined ether solutions are washed with water and a solution of sodium chloride, dried over sodium sulfate and the solvent evaporated completely in vacuo. The oily residue was further purified by chromatography on silica gel (eluant: diethylether hexane 1:7) to obtain pure 1-benzyl-4-(3-methyl-3-isopropoxy-propyl-1-oxy)-benzene, $n_D^{20}$: 1,5380.

EXAMPLE 2

The solution of 5 g of 4-cyclohexyl-1-(6-methyl-5-heptenyl-2-oxy)-benzene in 10 ml of absolute methanol was added in 10 minutes, with vigorous stirring, to a suspension cooled to −2° C of 5.6 g of pulverised mercury-(II)-acetate in 30 ml of absolute methanol. A slight temperature rise was detectable. Forty minutes after the addition of the alkene, additions were made, to the reaction mixture at −2° C, of 20 ml of 3N aqueous sodium hydroxide solution and, immediately afterwards, of 20 ml of a 0.5 molar sodium hydride solution in 3N sodium hydroxide solution, the temperature consequently rising to ca. 20°-23° C. Stirring was subsquently continued for 2 hours at 15° – 20° C. In further processing, the reaction mixture was decanted from the precipitated mercury, the overlying solution poured on 250 ml of saturated sodium chloride solution, and the whole extracted four times with diethyl ether. The combined ether solutions were washed with sodium chloride solution, dried over sodium sulphate, and the solvent completely removed in vacuo. The oily residue was further purified by chromatography on silica gel (eluant: diethyl ether/hexane 1:3) to obtain pure 4-cyclohexyl-1-(6-methyl-6-methoxy-heptanyl-2-oxy)-benzene; $n_D^{20} = 1.5060$.

The following compounds are prepared in a manner analogous to that described in Example 1 and 2:

| Cpd. No. | | |
|---|---|---|
| 3 | 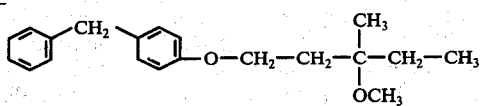 | $n_D^{20}$: 1,5425 |
| 4 | 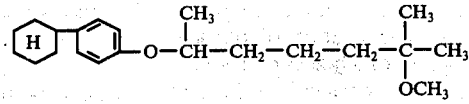 | $n_D^{20}$: 1,5055 |

-continued

| # | Structure | |
|---|---|---|
| 5 | Ph-CH$_2$-C$_6$H$_4$-O-CH$_2$-CH$_2$-C(CH$_3$)$_2$-O-CH$_2$-CH$_3$ | $n_D^{20}$: 1,5365 |
| 6 | H-Ph-C$_6$H$_4$-O-CH$_2$-CH$_2$-C(CH$_3$)$_2$-O-CH$_2$-CH$_3$ | $n_D^{20}$: 1,5059 |
| 7 | Ph-CH$_2$-C$_6$H$_4$-O-CH$_2$-CH$_2$-CH$_2$-O-CH$_2$-CH$_3$ | $n_D^{20}$: 1,5449 |
| 8 | Ph-CH$_2$-C$_6$H$_4$-O-CH$_2$-CH$_2$-CH(CH$_3$)-O-CH$_2$-CH$_3$ | $n_D^{20}$: 1,5361 |
| 9 | Ph-CH$_2$-C$_6$H$_4$-O-CH$_2$-CH$_2$-CH(CH$_3$)-O-CH$_3$ | $n_D^{20}$: 1,5450 |
| 10 | Ph-CH$_2$-C$_6$H$_4$-O-CH$_2$-CH$_2$-C(CH$_3$)$_2$-CH$_3$ | $n_D^{20}$ = 1,5389 |
| 11 | Ph-C$_6$H$_4$-O-CH$_2$-CH(CH$_3$)-C-CH$_2$-CH$_3$ | M.P. = 60–62° C |
| 12 | Ph-CH$_2$-C$_6$H$_4$-O-CH$_2$-CH=CH, with Cl substituents | $n_D^{20}$ = 1,5874 |
| 13 | Ph-CH$_2$-C$_6$H$_4$-O-CH$_2$-CH=C(Cl)(CH$_3$) | $n_D^{20}$ = 1,5752 |
| 14 | Ph-CH$_2$-C$_6$H$_4$-O-CH$_2$-CH=CH-Cl | $n_D^{20}$ = 1,5810 |
| 15 | H-Ph-C$_6$H$_4$-O-CH$_2$-CH=C(CH$_3$)-CH$_2$-CH$_3$ | $n_D^{20}$ = 1,5280 |
| 16 | H-Ph-C$_6$H$_4$-O-CH(CH$_3$)-CH$_2$-CH$_2$-CH=C(CH$_3$)$_2$ | $n_D^{20}$ = 1,5142 |

EXAMPLE 3

Contact effect on Aëdes aergypti larvae 20 about 2-day-old larvae of the yellow fever mosquito (Aëdes aegypti) were placed into a beaker containing a solution of the active substance (concentration 5 ppm). The beaker was then covered with a perforated lid. After the untreated control insects had completed moulting into the adult stage, the test insects were examined to determine the percentage of normal adults developed compared with the number in the control test.

All before mentioned compounds specified on pages 20–24 prepared according to example 1 and 2 exhibited a high degree of reduction of the development of normal adults or no development of normal adults at all.

EXAMPLE 4

Contact effect on Dysdercus-fasciatus-larvae

An amount of a 0.1% acetonic solution of the active substance corresponding to 10 mg of active substance per $m^2$ was measured by pipet into an aluminium dish and evenly distributed. After evaporation of the acetone, 10 larvae of the 5th stage of Dysdercus fasciatus were placed into the treated dish containing feed and moist cotton wool. The dish was then covered with a perforated lid. After ca. 10 days, i.e. as soon as the control insects had completed moulting into the adult stage, the test insects were examined to determine the number of normal adults in comparison with the non treated control.

All before mentioned compounds specified on pages 20–24 prepared according to Example 1 and 2 exhibited a high degree of reduction of development of normal adults or no development at all.

EXAMPLE 5

Contact action on Tenebrio molitor pupae

An amount of a 0,1% solution of active substance in acetone corresponding to 10 mg of active substance $m^2$ was pipetted into an aluminium dish and evenly distributed.

After the acetone had evaporated, 10 freshly shed pupae were laid on the treated surface. The dish was covered with a sieve cover.

After the untreated controls had left their cocoons as Imagines the test subjects were examined for the number of normal adults compared with the number in the control test.

All before mentioned compounds specified on pages 20–24 prepared according to Example 1 and 2 showed a high degree of reduction of the development of normal adults or no development at all.

EXAMPLE 6

Action against spider mites

Busch bean plants (*Phaseolus vulgaris*) in the 2-leaf stage were infested with spider mites, 12 hours before the treatment with the active substance, by placing attacked pieces of leaf from a culture on them, so that after the end of this time a population in all stages of development was present on the plant. The plants were then sprayed with the emulsified active substance (concentration 0,04%) by means of a chrmatography atomiser, until a uniform deposit of droplets was produced on the surface of the leaf. The results were assessed after 2 and 7 days; the parts of the plant were inspected under a stereo-microscope in order to calculate the percentages of destruction.

The percentages of destruction of the normally sensitive variety Tetranychus urticae Koch and of the phosphoric acid ester-tolerant variety Tetranychus telarius L. are determined. All before mentioned compounds specified on pages 20–24 prepared according to example 1 and 2 showed a high degree of reduction of the parasites or complete destruction.

EXAMPLE 7

Action against *Spodoptera littoralis*

Lattuce leaves are dipped into a 1% acetonic solution of the active substance and subsequently dried. 10 larvae ($L_3$-$L_4$ stage) are placed on each of two leaves each in a separate Petri dish. The puppae developed from the larvae are transferred to a container. Evaluation is made in accordance with the number of normal adults.

All before mentioned compounds specified on pages 20–24 prepared according to Example 1 and 2 exhibited a high degree of reduction of development of normal adults or no development at all.

What we claim is:
1. 4-Benzyl-1-(3-Chloro-2-propenyl-1-oxy)-benzene.
2. 4-Cyclohexyl-1-(3-methyl-2-pentenyl-1-oxy)-benzene.
3. 4-benzyl-1-(2,3-dichloro-2-propenyl-1-oxy) benzene.

* * * * *